US011311633B2

(12) United States Patent
Zolotukhin et al.

(10) Patent No.: US 11,311,633 B2
(45) Date of Patent: Apr. 26, 2022

(54) SATIATION PEPTIDES FOR WEIGHT LOSS AND ALTERED TASTE SENSITIVITY

(71) Applicant: University of Florida Research Foundation, Incorporated, Gainesville, FL (US)

(72) Inventors: Sergei Zolotukhin, Gainesville, FL (US); Sean M. Crosson, Gainesville, FL (US); Cedrick Shawn Dotson, Gainesville, FL (US); Seth Currlin, Gainesville, FL (US); Andres Acosta, Rochester, MN (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 169 days.

(21) Appl. No.: 15/489,717

(22) Filed: Apr. 17, 2017

(65) Prior Publication Data

US 2017/0326257 A1 Nov. 16, 2017

Related U.S. Application Data

(60) Provisional application No. 62/323,690, filed on Apr. 16, 2016.

(51) Int. Cl.

| | | |
|---|---|---|
| *A61K 38/22* | (2006.01) | |
| *A61K 38/26* | (2006.01) | |
| *C07K 14/47* | (2006.01) | |
| *C07K 14/575* | (2006.01) | |
| *C07K 14/605* | (2006.01) | |
| *A61K 48/00* | (2006.01) | |
| *A61K 9/00* | (2006.01) | |
| *C12N 15/86* | (2006.01) | |

(52) U.S. Cl.
CPC ........ *A61K 48/0075* (2013.01); *A61K 9/0053* (2013.01); *A61K 38/22* (2013.01); *A61K 38/2207* (2013.01); *A61K 38/26* (2013.01); *A61K 48/0058* (2013.01); *C07K 14/47* (2013.01); *C07K 14/575* (2013.01); *C07K 14/57563* (2013.01); *C07K 14/605* (2013.01); *C12N 15/86* (2013.01); *C12N 2750/14142* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,671,953 A | 6/1987 | Stanley et al. | |
| 5,912,227 A | 6/1999 | Croom et al. | |
| 6,106,844 A | 8/2000 | King | |
| 6,177,096 B1 | 1/2001 | Zerbe et al. | |
| 6,998,387 B1 | 2/2006 | Goke et al. | |
| 7,459,432 B2 | 12/2008 | Cowley et al. | |
| 8,058,233 B2 * | 11/2011 | Cowley .............. | A61K 38/1709 514/5.2 |
| 8,202,836 B2 | 6/2012 | Moore et al. | |
| 8,273,713 B2 | 9/2012 | Pittner et al. | |
| 9,492,505 B2 * | 11/2016 | Zolotukhin .......... | A61K 9/0019 |
| 2004/0086579 A1 | 5/2004 | Higgins et al. | |
| 2005/0009748 A1 | 1/2005 | Dinh et al. | |
| 2006/0014678 A1 | 1/2006 | Cowley et al. | |
| 2007/0275893 A1 | 11/2007 | Quay | |
| 2008/0015265 A1 | 1/2008 | Rubin et al. | |
| 2008/0254108 A1 | 10/2008 | Rosenberg | |
| 2009/0004224 A1 | 1/2009 | Steward et al. | |
| 2011/0070287 A1 | 3/2011 | Nielsen et al. | |
| 2011/0092416 A1 | 4/2011 | Doyle et al. | |
| 2012/0035100 A1 * | 2/2012 | Zolotukhin .......... | A61K 9/0056 514/4.9 |
| 2014/0199272 A1 * | 7/2014 | Chiorini ................. | C07K 14/48 424/93.6 |
| 2017/0080056 A1 | 3/2017 | Zolotukhin et al. | |
| 2019/0224280 A1 | 7/2019 | Acosta et al. | |
| 2019/0231850 A1 | 8/2019 | Acosta et al. | |
| 2020/0061158 A1 | 2/2020 | Zolotukhin et al. | |

FOREIGN PATENT DOCUMENTS

| | | | |
|---|---|---|---|
| WO | WO 2003/026591 A2 | | 4/2003 |
| WO | WO 2003/057170 A2 | | 7/2003 |
| WO | WO 2005/080433 A2 | | 9/2005 |
| WO | WO 2005/110467 A1 | | 11/2005 |
| WO | WO 2008/109068 A2 | | 9/2008 |
| WO | WO 2017/009236 | * | 1/2017 |

OTHER PUBLICATIONS

Fagoe et al. (Gene Therapy (2014) 21, 242-252) (Year: 2014).*
Baggio et al. (Gastroenterology 2004;127:546-558) (Year: 2004).*
Moran et al. (Am J Physiol. May 1982;242(5):R491-7) (Year: 1982).*
Healthline (downloaded on Apr. 3, 2020 from URL:<https://www.healthline.com/health/salivary-gland-biopsy>) (Year: 2020).*
Gupta (Indian J Endocrinol Metab. May-Jun. 2013; 17(3): 413-421) (Year: 2013).*
International Search Report and Written Opinion for International Application No. PCT/US2010/021677 dated Oct. 22, 2010.
International Preliminary Report on Patentability for International Application No. PCT/US2010/021677 dated Aug. 4, 2011.
Baggio et al., Oxyntomodulin and glucagon-like peptide-1 differentially regulate murine food intake and energy expenditure. Gastroenterology. Aug. 2004;127(2):546-58.
Fazen, et al. "Oral Delivery of the Appetite Suppressing Peptide hPYY(3-36) through the Vitamin $B_{12}$ Uptake Pathway"; J. Med. Chem; 2011;54(24):8707-8711.

(Continued)

*Primary Examiner* — Sergio Coffa
(74) *Attorney, Agent, or Firm* — Wolf, Greenfield & Sacks, P.C.

(57) ABSTRACT

The present application provides methods and compositions for AAV-mediated delivery of PYY and Glucagon-like Peptide 1 or an analog thereof (e.g., Exendin-4) to a subject (e.g., the saliva of a subject). In some embodiments, compositions and methods for topical delivery of Ex-4 and PYY peptides also are provided. Methods and compositions are useful to promote weight loss and/or altered lipid taste sensitivity, as well as for the treatment of diabetes.

18 Claims, 8 Drawing Sheets

Specification includes a Sequence Listing.

(56) References Cited

OTHER PUBLICATIONS

Hurtado, et al.; "Salivary Peptide Tyrosine-Tyrosine 3-36 Modulates INgestive Behavior without Inducing Taste Aversion"; The Journal of Neuroscience; 2013; 33(47):18368-18380.
Steinert et al. "Oral administration of glucagon-like peptide 1 or peptide YY 3-36 affects food intake in healthy male subjects [1-3]"; Am J. Clin Nutr; 2010; 92: 810-817.
Wank, G Protein-coupled receptors in gastrointestinal physiology I. CCK receptors: an exemplary family. Am J Physiol. Apr. 1998;274(4 Pt 1):G607-13.
U.S. Appl. No. 16/562,382, filed Sep. 5, 2019, Zolotukhin et al.

\* cited by examiner

SATIATION PEPTIDES FOR WEIGHT LOSS AND ALTERED TASTE SENSITIVITY

RELATED APPLICATIONS

This application claims the benefit under 35 U.S.C. § 119(e) of U.S. Provisional Patent Application No. 62/323,690, filed Apr. 16, 2016, entitled "SATIATION PEPTIDES FOR WEIGHT LOSS AND ALTERED TASTE SENSITIVITY," the entire contents of which are incorporated herein by reference.

FEDERALLY SPONSORED RESEARCH

This invention was made with government support under grant number DC012819 awarded by the National Institutes of Health. The government has certain rights in the invention.

BACKGROUND OF INVENTION

Current treatments for obesity involve stimulant medications which are mildly effective and can have detrimental side effects if used long-term. Other current treatment methods involve invasive bariatric surgery which, while sometimes effective, can involve a variety of serious complications. More recently, satiation gut peptides have been investigated as potential treatments for obesity. These peptides are secreted from the small intestine and colon in response to food intake. Penetrating from plasma through the blood-brain barrier, they act by activating specific receptors in the satiety center of the hypothalamus thus inducing satiation. Some of the most important satiation gut peptides are Peptide YY (PYY), Glucagon-like Peptide 1 (GLP-1), oxyntomodulin, and cholecystokinin. Acute supplemental therapy with satiation gut peptides reduces food intake and body weight in obese animal models as well as in lean and obese human subjects. Studies using satiation peptide supplement therapy by intravenous injection prior to meals have been conducted, because it was believed that oral administration would be unsuccessful due to likely peptide breakdown by enzymes and acids prior to reaching the blood.

SUMMARY OF INVENTION

Aspects of the application relate to methods and compositions for delivering a combination of PYY and GLP-1 or an analog thereof (e.g., exendin-4 (EX-4)) to a subject (e.g., to the mouth of a subject). In some embodiments, a combination of PYY and GLP-1 or an analog thereof provide persistent weight loss with greater efficacy that current drugs. In some embodiments, nucleic acid mediated (e.g., AAV-mediated) delivery methods are used to deliver GLP-1 or an analog thereof (e.g., Ex-4) and PYY to a subject (e.g., to the saliva of a subject). In some embodiments, both PYY and GLP-1 or an analog thereof are delivered in the form of peptide compositions. In some embodiments, PYY and GLP-1 or an analog thereof are delivered topically. In some embodiments, combinations of PYY and GLP-1 or an analog thereof (e.g., Ex-4) provide persistent weight loss with greater efficacy than current drugs, or prevent weight gain, in a subject, while avoiding the risks of surgery. In some embodiments, combinations of PYY and GLP-1 or an analog thereof (e.g., EX-4) are particularly useful in the treatment of diabetes. Aspects of the present application also relate to modulation of body weight in mammals using recombinant Adeno-associated viral (rAAV) vector(s) expressing GLP-1 or an analog thereof (e.g., Ex-4) and PYY. However, other nucleic acid vectors (e.g., cDNA) or other viral vectors may be used, and/or direct peptide administration also may be used to deliver PYY and GLP-1 or an analog thereof to a subject (e.g., a mammalian subject, for example a human). In some embodiments, viral vectors, nucleic acids, and/or peptides can be administered to the mouth, the tongue, the throat, the parotid glands, the sublingual glands, or the submandibular salivary glands. In some embodiments, a combination of PYY and GLP-1 or an analog thereof (e.g., Ex-4), either by gene expression or topical administration can be used in the treatment of diabetes. Accordingly, aspects of the present application relate to topical administration of satiation peptides, for example via delivery to the mouth of a subject of viral vectors or nucleic acids encoding the peptides or via delivery to the mouth of a subject of the peptides themselves, or combinations thereof.

In some embodiments, aspects of the disclosure relate to methods of inducing satiation in a subject comprising applying a satiation gut peptide composition (e.g., PYY and Ex-4), comprising peptides, nucleic acids (e.g., cDNA), vectors (e.g., viral vectors such as adeno-associated virus (AAV)), or any combination thereof, to the mouth, tongue, salivary glands, or throat of the subject. In some embodiments, said application comprises spraying a fluid composition comprising a satiation gut peptide composition into the mouth of the subject such that said composition contacts a tongue of the subject. In some embodiments, said application occurs a period of time prior to eating. In some embodiments, said satiation gut peptide composition also comprises one or more of oxyntomodulin or cholecystokinin.

In some embodiments, aspects of the disclosure include compositions comprising satiation gut peptides PYY and Ex-4. In some embodiments, a satiation gut peptide composition (e.g., comprising one or more nucleic acids or viral vectors encoding satiation gut peptides, and/or the peptides) is delivered via direct injection. In some embodiments, said composition is in a dosage form for topical delivery. In some embodiments, said dosage form is a spray. In some embodiments, said dosage form is a lozenge. In some embodiments, said dosage form is an orally disintegrating tablet. In some embodiments, said dosage form is an oral dissolvable film or dissolvable planar sheet. In some embodiments, said composition is in an oral dosage form. In some embodiments, one or more additional satiation gut peptides can be administered to the subject.

In some embodiments, aspects of the disclosure include a vector comprising an expression cassette that includes a polynucleotide sequence that encodes two or more satiation gut peptides. In some embodiments, said expression cassette transfects salivary gland cells.

In some embodiments, aspects of the disclosure also include methods of increasing satiation gut peptide concentration (e.g., of PYY and Ex-4) in the saliva of a subject, comprising delivering a vector to a cell of said subject, wherein said satiation gut polynucleotide sequence, peptide, viral vector, or cDNA is expressed. In some embodiments, the satiation gut peptide concentration in the plasma of said subject remains unchanged or decreases.

Aspects of the disclosure include methods of inducing satiation in a subject comprising administering to a subject a recombinant adeno-associated viral vector (rAAV) expressing a satiation gut peptide composition.

In some embodiments, said recombinant adeno-associated viral vector is of serotype 8. In some embodiments, wherein said recombinant adeno-associated viral vector is of serotype 5. In some embodiments, said recombinant adeno-associated viral vector is administered to the mouth, tongue, salivary glands, or throat of the subject.

Aspects of the disclosure include methods of inducing satiation in a subject by administering to the subject a recombinant adeno-associated viral vector expressing two or more satiation gut peptides. In some embodiments, said satiation gut peptide is selected from the group consisting of: PYY, GLP-1, Oxyntomodulin, Cholecystokinin, Exendin-4, and a combination of PYY and Exendin-4. In some embodiments, said recombinant adeno-associated viral vector comprises a dual PYY-Ex-4 vector.

Aspects of the application relate to methods of inducing satiation in a subject comprising applying a satiation gut peptide composition to the mouth, the tongue, the throat, the parotid glands, sublingual glands, or submandibular salivary glands of the subject. In some embodiments, the satiation gut peptide composition delivered include a peptide tyrosine tyrosine (PYY) peptide and an Exendin-4 (Ex-4) peptide. In some embodiments, the gut peptide composition (e.g., PYY and Ex-4) are both in a single composition. In some embodiments, the gut peptide composition (e.g., PYY and Ex-4) are in separate compositions. In some embodiments, the gut peptides are delivered by administration of a nucleic acid encoding PYY and Ex-4. In some embodiments, the gut peptides are delivered by administration of the PYY and Ex-4 peptides. In some embodiments, the PYY and Ex-4 are delivered by administration of a PYY peptide and a nucleic acid encoding Ex-4. In some embodiments, the PYY and Ex-4 are delivered by administration of a peptide Ex-4 and a nucleic acid encoding PYY. In some embodiments, the PYY and Ex-4 are delivered by administration of PYY and Ex-4 cDNA. In some embodiments, PYY and Ex-4 are delivered by administration of a viral vector encoding PYY and a nucleic acid encoding Ex-4. In some embodiments, PYY and Ex-4 are administered separately encoded by any combination of nucleic acid, peptide, cDNA, or viral vector. In some embodiments, PYY is administered first, and Ex-4 is administered second. In some embodiments, Ex-4 is administered first and PYY is administered second. In some embodiments, PYY-Ex-4 dual vectors are administered more than once. In some embodiments, PYY-Ex-4 dual vectors are administered 2, 3, 4, 5, 6, 7, 8, 9, or 10 times. In some embodiments, the viral vector is an adeno-associated virus (AAV).

In some embodiments, aspects of the invention also relate to the treatment or prevention, of obesity and/or diabetes. The surprising synergistic combination of PYY and Ex-4 can also be used to regulate weight loss and/or altered lipid taste sensitivity. In some embodiments, oxyntomodulin and/or cholecystokinins are also delivered with PYY and Ex-4 to the subject.

BRIEF DESCRIPTION OF DRAWINGS

FIG. 4A shows one hour food intake after one spray with PYY, 5 μg per 100 g of body weight vs. spray with sterile H2O. FIG. 4B shows the difference in one hour food intake after PYY mouth spray vs. sterile H2O, shown are individual animals. FIG. 4C shows dose response of PYY mouth spray on FI as measured after one hour. FIG. 4D shows 24 hour food intake after PYY mouth spray vs. sterile H2O. *P<0.05, **P<0.01.

FIG. 7 shows confocal microscopy imaging of eGFP expression in WT C57BL/6 mouse 2 weeks after AAV8-GFPsc administration via salivary gland ductile cannulation. FIG. 7A shows eGFP expression in fixed frozen mouse submandibular gland sections, and FIG. 7B shows fixed frozen liver sections.

DETAILED DESCRIPTION OF INVENTION

Figure 1:
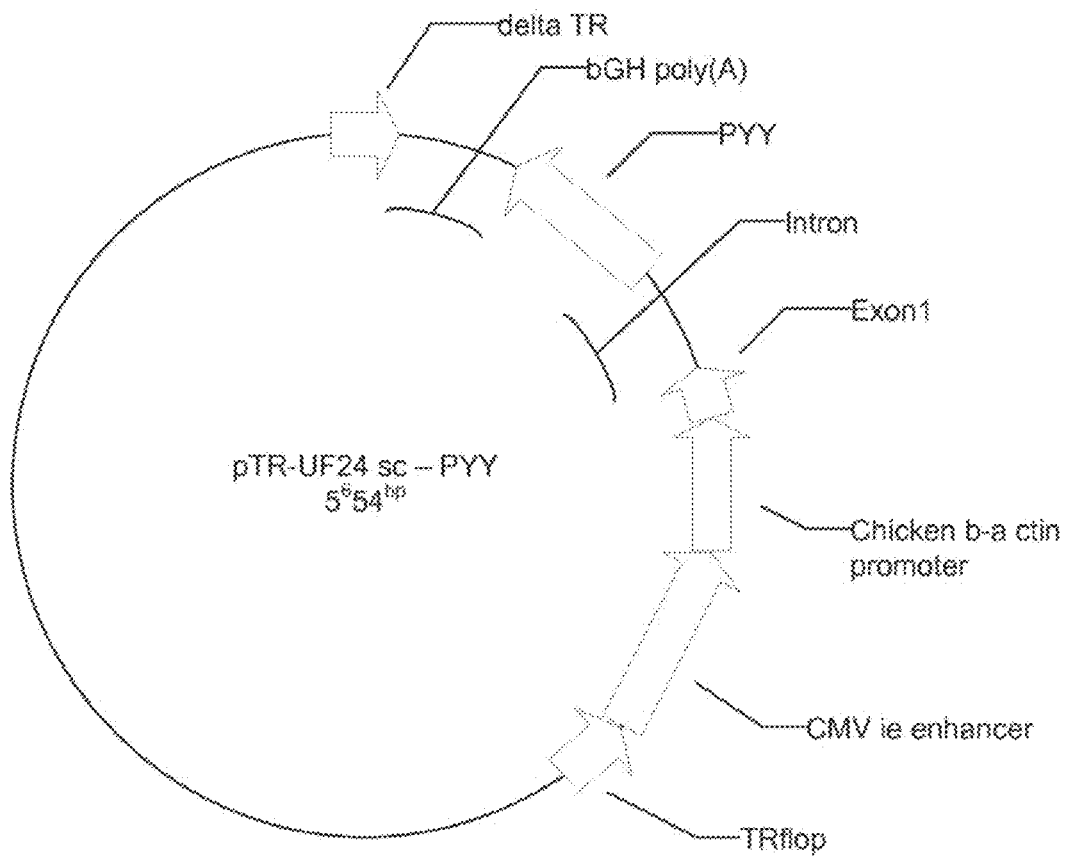
FIG. 1 illustrates a non-limiting embodiment of a rAAV-PYY vector plasmid comprising a TR (a terminal repeat), CMV (cytomegalovirus) enhancer, and CBA (Chicken B actin) promoter.

In some embodiments, aspects of the application relate to methods and compositions for inducing satiation in a subject by delivering a satiation gut peptide composition (e.g., a PYY and GLP-1 or analog thereof) to a subject (e.g., to the mouth of the subject). In some embodiments, the satiation gut peptides delivered include a PYY peptide and an Ex-4 peptide. In some embodiments, the gut peptides are delivered by administration of a nucleic acid encoding PYY and Ex-4. In some embodiments, the gut peptides are delivered by administration of the PYY and Ex-4 peptides themselves. In some embodiments, the PYY and Ex-4 are delivered by administration of a PYY peptide and a nucleic acid encoding Ex-4. In some embodiments, the PYY and Ex-4 are delivered by administration of an Ex-4 peptide and a nucleic acid encoding PYY. In some embodiments, the PYY and/or Ex-4 are delivered by administration of PYY and Ex-4 encoding nucleic acids, for example RNA, DNA, or cDNA. In some embodiments, a recombinant nucleic acid molecule that encodes both PYY and Ex-4 is used. In some embodiments, two separate recombinant nucleic acids are used, one of which encodes PYY and one of which encodes Ex-4. In some embodiments, PYY and/or Ex-4 are delivered by administration of a viral vector encoding PYY and/or Ex-4. In some embodiments, a viral vector that encodes both PYY and Ex-4 is used. In some embodiments, two separate viral vectors are used, one of which encodes PYY and one of which encodes Ex-4. In some embodiments, a viral vector is a recombinant adeno-associated viral vector (rAAV vector).

In some embodiments, aspects of the application relate to the treatment of obesity and/or diabetes based on the synergistic effect of PYY and Ex-4. The surprising synergistic effect of PYY and Ex-4 can also be used to regulate weight loss and/or altered lipid taste sensitivity. In some embodiments, oxyntomodulin and/or cholecystokinins are also delivered along with PYY and Ex-4.

In some embodiments, PYY and Ex-4 are administered separately (e.g., as peptides and/or encoded by any combination of nucleic acid or viral vector). In some embodiments, PYY is administered first, and Ex-4 is administered second. In some embodiments, Ex-4 is administered first and PYY is administered second. In some embodiments, PYY-Ex-4 dual vectors are administered more than once. In some embodiments, PYY-Ex-4 dual vectors are administered 2, 3, 4, 5, 6, 7, 8, 9, or 10 times.

Peptide tyrosine tyrosine (PYY) and glucagon-like peptide 1 (GLP-1) are gastrointestinal peptides secreted into the circulation in response to nutrient uptake. Salivary GLP-1 has also been implicated in satiation as its cognate receptor, GLP-1 receptor, has been shown to be expressed on taste bud associated nerve fibers. Although PYY and GLP-1 have been studied individually as obesity therapies, the combined effects of these peptides on weight loss and food intake when administered together, particularly in the saliva of a subject, was not known. Exendin-4, a hormone found in the saliva of the Gila monster, is a GLP-1 agonist. Oxyntomodulin is a peptide hormone, that has been found to suppress appetite. Cholecystokinin is a peptide hormone of the gastrointestinal system responsible for stimulating the digestion of fat and protein.

In some embodiments, aspects of the application relate to delivering PYY and a GLP-1 analog (e.g., Ex-4) to a subject. In some embodiments, aspects of the application comprise the use of recombinant adeno-associated viral (rAAV) vectors to deliver PYY and Exendin-4 transgenes to the mouth of a subject (e.g., to submandibular salivary glands) simultaneously. In some embodiments, aspects of the application comprise the use of rAAV vectors to deliver PYY and Ex-4 transgenes to the mouth of a subject (e.g., to submandibular salivary glands) separately. Ex-4 is a GLP-1 analog resistant to proteolytic degradation. In some embodiments, delivery of the satiation gut peptides can be delivered using any of the following techniques: direct nucleic acid (e.g., cDNA) delivery, viral vector delivery, direct peptide delivery, or any combination of these therapies.

In some embodiments, a viral vector may be in the form of an rAAV nucleic acid encoding one or both of PYY and a GLP-1 or analog thereof, wherein the rAAV nucleic acid is encapsidated in an rAAV particle. The rAAV particle may be of any AAV serotype (e.g., 1, 2, 3, 3B, 4, 5, 6, 7, 8, 9, 10, etc.), including any derivative (including non-naturally occurring variants of a serotype) or pseudotype.

As described herein, in some embodiments nucleotides that encode satiation gut peptides can be used along with or separately from direct delivery of peptides (e.g., alone). Satiation gut peptides include peptides such as Peptide YY, GLP-1, oxyntomodulin, exendin-4, and cholecystokinin. Nucleotides and peptides having substantial identity to the nucleotide and/or amino acid sequences of peptide YY, GLP-1, exendin-4, oxyntomodulin, and cholecystokinin also are contemplated for use in accordance with the teachings herein.

Examples of PYY sequences include NM_004160.5, NC_000077.6, NP_663410.1, CAG46926.1, XP_004041595, JAA33294.1, NP_004151.3 or a variant thereof. In some embodiments, the PYY sequence has at least 60%, at least 70%, at least 80%, at least 90%, or at least 95% identity to NM_004160.5, NC_000077.6, NP_663410.1, CAG46926.1, XP_004041595, JAA33294.1, or NP_004151.3. In some embodiments, the PYY peptide is a human PYY peptide. In some embodiments, the human PYY peptide has an amino acid sequence as shown in SEQ ID NO: 1. In some embodiments, the human PYY peptide is shown as SEQ ID NO: 7, SEQ ID NO: 8 or SEQ ID NO: 9 or a variant thereof. In some embodiments, an abbreviated sequence or functional fragment of the human PYY peptide is used. In some embodiments, the human PYY peptide fragment is SEQ ID NO: 2. In some embodiments, the oxyntomodulin has a sequence as shown in SEQ ID NO: 3. In some embodiments, the oxyntomodulin sequence has at least 60%, at least 70%, at least 80%, at least 90%, or at least 95% identity to SEQ ID NO: 3. In some embodiments, GLP-1 sequences include those embodied in U.S. Pat. Nos. 5,631,224, 6,191,102, and 6,998,387, the sequence description of which is incorporated by reference herein. Examples of Ex-4 sequences include GenBank sequences AAB22006.1, P26349.2, and/or P43220.2. In some embodiments, the Ex-4 is HGEGTFTSDL SKQMEEEAVR LFIEWLKNGG PSSGAPPPS (SEQ ID NO: 10) or a variant thereof. In some embodiments, the Ex-4 sequence has at least 60%, at least 70%, at least 80%, at least 90%, or at least 95% identity to AAB22006.1 (SEQ ID NO: 10), P26349.2, and/or P43220.2. In some embodiments, the cholecystokinin sequence has a sequence comprising SEQ ID NO: 4, SEQ ID NO: 5 or SEQ ID NO: 6. In some embodiments, the cholecystokinin sequence has at least 60%, at least 70%, at least 80%, at least 90%, or at least 95% identity to SEQ ID NO: 4, SEQ ID NO: 5 or SEQ ID NO: 6.

In some embodiments, aspects of the application relate to establishing a stable and longer-term delivery of satiation gut peptides (e.g., PYY and GLP-1 or an analog thereof) and/or administration of gut peptides intended for targeting specific areas of the body which now have been identified as effecting an unexpectedly favorable satiation response. According to certain embodiments, the invention pertains to compositions and methods for treating obesity involving satiation gut peptide administration to the mouth of a subject. According to one specific embodiment, the subject invention pertains to providing a long-term increase of satiation peptides in the saliva by targeting salivary glands with vectors, viral vectors, adenoviral vectors, or other suitable vectors for transfection of cells in a human or non-human animal, harboring the respective gene(s), for introduction and expression in targeted cells.

Aspects of the disclosure also include methods of inducing satiation in a subject comprising applying a satiation gut peptide to the mouth of the subject. In some embodiments, said application comprises spraying a fluid composition comprising a satiation gut peptide into the mouth of the subject such that said composition contacts a tongue of the subject. In some embodiments, said application occurs a period of time prior to eating.

In some embodiments, the application pertains to a method of inducing satiation in a subject that includes applying to at least a portion of the mouth of the subject that includes applying to at least a portion of the mouth of the subject a composition comprising satiation gut peptides at a time period prior to eating (pre-prandial). The time period may be 5 seconds or more. In a specific embodiment, the time period is 5-360 minutes prior to eating. In a more specific embodiment, the time period is 30-120 minutes prior to eating. In some embodiments, the peptides are delivered to the mouth and/or pharynx to a subject according to a generally continuous time period of at least 5, 10, 15 or more seconds. In another embodiment, the delivery is for 0.1-120 mins, including any specific 0.1 minute increment within such range. In a specific embodiment, it has been found that administration of the peptides such that they are in prolonged contact with the tongue is optimal.

In some embodiments, the application relates to a container that comprises a solid (e.g., powder), fluid or semifluid composition that comprises satiation gut peptides and a pharmaceutically acceptable carrier. In a specific embodiment, the container comprises a nozzle for ejecting or spraying the composition into the mouth of the subject. The container may be under pressure and/or be equipped with a pump nozzle.

In some embodiments, the application relates to a mouth applicable article loaded with satiation gut peptides. The article may be chewing gum loaded with peptides, a lozenge (e.g., a dissolvable solid or semi-solid object intended to hold in the mouth for a period of time) loaded with peptides, a permeable pouch or sponge loaded with peptides, or an orally dissolvable film loaded with peptides. The article can be designed for extended delivery of peptides to the mouth and/or pharynx, as opposed to the conventional oral administration that involves the immediate swallowing of a pill, tablet or fluid composition as is a conventionally understood as oral administration. In particular, the article can be designed for delivery to the tongue.

In some embodiments, cells related to the mouth such as mucosal or salivary gland cells are transformed with vectors engineered to express and release a satiation gut peptides.
Adeno-Associated Virus-Based Vectors.

In some embodiments, nucleic acid(s) encoding PYY and/or GLP-1 or an analog thereof (e.g., Ex-4) are delivered via a viral vector, for example an rAAV vector. In some embodiments, the serotype of the rAAV is serotype 8. In some embodiments, the serotype of the rAAV is serotype 5. In some embodiments, said recombinant adeno-associated viral vector is administered to the submandibular salivary gland, the parotid gland, and/or the sublingual gland of a subject (e.g., a mammal, for example a human).

The adeno-associated viruses (AAV) are DNA viruses of relatively small size which can integrate, in a stable and site-specific manner, into the genome of the cells which they infect, but that also can persists in an non-integrated form in infected cells. AAV are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see PCT Publications No. WO 91/18088 and WO 93/09239; U.S. Pat. Nos. 4,797,368 and 5,139,941; EP Publication No. 488 528). Replication defective rAAVs for delivering recombinant nucleic acids can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (e.g., an adenovirus). The AAV recombinants which are produced are then purified by standard techniques.

The ITR sequences of a nucleic acid or nucleic acid vector described herein can be derived from any AAV serotype (e.g., 1, 2, 3, 4, 5, 6, 7, 8, 9, or 10) or can be derived from more than one serotype. In some embodiments of the nucleic acid or nucleic acid vector provided herein, the ITR sequences are derived from AAV2. In some embodiments of the nucleic acid or nucleic acid vector provided herein, the ITR sequences are derived from AAV5. In some embodiments of the nucleic acid or nucleic acid vector provided herein, the ITR sequences are derived from AAV8. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Calif.; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962, 313, all of which are incorporated herein by reference).

Methods for constructing and using viral vectors are known in the art (see, e.g., Miller and Rosman, BioTechniques 1992, 7:980-990). In accordance with the present application there may be employed conventional molecular biology, microbiology, and recombinant DNA techniques within the skill of the art. Such techniques are well-known and are explained fully in the literature. See, e.g., Sambrook, Fritsch and Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector (e.g., as a plasmid) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, aspects of the disclosure include methods of inducing satiation in a subject comprising administering to a subject a recombinant adeno-associated viral vector expressing two or more satiation gut peptides (e.g., PYY and a GLP-1 or analog thereof). In some embodiments, said recombinant adeno-associated viral vector comprises a dual PYY-Ex-4 vector. In some embodiments, delivery of the satiation gut peptide composition is to the mouth, the tongue, the throat, parotid gland, sublingual gland, or submandibular salivary gland of the subject. In some embodiments, the delivery method comprises injection, topical delivery, or other methods of delivery to the mouth, including but not limited to sprays, lozenges, orally disintegrating tablets, oral dissolvable films or dissolvable planar sheets, and/or other oral dosage forms. In some embodiments, the method of delivery allows for transduction of the satiation gut peptide encoding compositions (e.g., PYY and a GLP-1 or analog thereof) to the salivary glands (e.g., parotid, submandibular, and/or sublingual glands).

In some embodiments, nucleic acids that encode one or both of the satiation gut peptides of interest can be delivered directly (e.g., in the form of a nucleic acid that is not encapsidated in a viral particle) to the mouth of a subject via any of the routes described above or elsewhere in this application for the rAAV particles. In some embodiments, the method of delivery allows for transfection of the satiation gut peptide encoding compositions (e.g., PYY and a GLP-1 or analog thereof) to the salivary glands (e.g., parotid, submandibular, and/or sublingual glands).

In some embodiments, a nucleic acid (e.g., a viral vector or a nucleic acid that is not encapsidated in a viral particle) that encodes one or more satiation peptides (e.g., PYY and a GLP-1 or analog thereof, for example Ex-4) comprises a promoter that is operably connected to coding sequence(s) for one or both (or more) satiation peptides of interest. In some embodiments, all the peptide coding sequences are operably connected to a single promoter. In some embodiments, each peptide coding sequence is operably connected to a separate promoter (e.g., on the same recombinant nucleic acid or on separate recombinant nucleic acids). In some embodiments, each promoter can independently be any suitable promoter, including, for example, a constitutive promoter, an inducible promoter, a mammalian promoter, a human promoter, a viral promoter, a microbial promoter, a tissue-specific promoter, a species-specific promoter, or a combination of two or more of the foregoing.

In some embodiments, proteins and polypeptide sequences, as well as polynucleotides encoding the same, having substantial identity with the sequences specifically described herein may be used in conjunction with the present invention (e.g., for the delivery of a polypeptide having substantial identity with a PYY polypeptide and/or for the delivery of a polypeptide having substantial identify with a GLP-1 polypeptide or analog thereof). Here, "substantial identity" means that two sequences, when optimally aligned such as by the programs GAP or BESTFIT (peptides) using default gap weights, or as measured by computer algorithms BLASTX or BLASTP, share at least 50%, 60%, 70%, preferably at least 75%, 80%, 85%, 90%, or 95% sequence identity, or sequence identity of any integer percentage between 50% and 99.9%. Preferably, residue positions which are not identical differ by conservative amino acid substitutions. For example, the substitution of amino acids having similar chemical properties such as charge or polarity are not likely to affect the properties of a protein. Non-limiting examples include glutamine for asparagine or glutamic acid for aspartic acid.

The term "variant" as used herein refers to nucleotide and polypeptide sequences wherein the nucleotide or amino acid sequence exhibits substantial identity with the nucleotide or amino acid sequences of SEQ ID NOs: 1-10, for example 50%, 60%, 70%, or 75% sequence identity, or preferably 80%, 85%, or 90-95% sequence identity to the sequences of the present application, provided said variant has a biological activity as defined herein. The variant may be arrived at by modification of the native nucleotide or amino acid sequence by such modifications as insertion, substitution or deletion of one or more nucleotides or amino acids or it may be a naturally occurring variant. The term "variant" also includes homologous sequences which hybridize to the sequences of the invention under standard or preferably stringent hybridization conditions familiar to those skilled in the art. Examples of the in situ hybridization procedure typically used are described in (Tisdall et al., 1999); (Juengel et al., 2000). Where such a variant is desired, the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed, using techniques standard in the art.

In specific embodiments, a variant of a polypeptide is one having at least about 80%, 85%, 90%, or 95% amino acid sequence identity with the amino acid sequence of a native full length sequence of a satiation gut peptide, or a fragment thereof, for example as described in this application (e,g., a PYY of SEQ ID NO: 1, 7, 8 or 9 and/or an Ex-4 of SEQ ID NO: 10) and known in the art. Such variant polypeptides include, for instance, polypeptides wherein one or more amino acid residues are added, or deleted, at the N- and/or C-terminus, as well as within one or more internal domains, of the full-length amino acid sequence. Fragments of the peptides are also contemplated. Ordinarily, a variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with a polypeptide encoded by a nucleic acid molecule described in this application or a specified fragment thereof. Ordinarily, variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, or more.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by those that: (1) employ low ionic strength and high temperature for washing, 0.015 M sodium chloride/0.0015 M sodium citrate/0.1% sodium dodecyl sulfate at 50° C.; (2) employ during hybridization a denaturing agent, 50% (v/v) formamide with 0.1% bovine serum albumin/0.1% Ficol/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" are identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An oral liquid formulation (e.g., for delivering a peptide molecule, a nucleic acid molecule, or a viral particle or a combination thereof) may, for example, be a pharmaceutically acceptable emulsion, syrup, elixir, suspension, solution and the like, which may contain a pharmaceutically customary inert diluent such as water and if desired, additives. Such an oral liquid formulation can be produced by mixing an active ingredient (e.g., PYY and/or Ex-4), inert diluent and other additives if necessary in accordance with a customary method. An oral formulation usually contains about 0.01 to 99% by weight, preferably about 0.1 to 90% by weight, usually about 0.5 to 50% by weight of an inventive active compound, although the amount may vary depending on the dosage form. In some embodiments, the oral liquid formulation comprises buffering agents, antioxidants, flavoring, solvents, cosolvents, sweeteners, preservatives, and/or dyes.

In some embodiments, the composition comprises a pharmaceutically acceptable carrier. The term "carrier" refers to a diluent, adjuvant, excipient, or vehicle with which the rAAV particle (and/or peptide and/or other nucleic acid) is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

Typically, such compositions may contain at least about 0.1% of the therapeutic agent (e.g., satiation peptides, nucleic acids encoding one or more satiation gut peptide compositions, or an rAAV particle) or more, although the percentage of the active ingredient(s) may, of course, be varied and may conveniently be between about 1 or 2% and about 70%, 80%, 90% or more of the weight or volume of the total formulation. Naturally, the amount of therapeutic agent(s) (e.g., rAAV particle, peptide, and/or nucleic acid composition) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, the compositions of rAAV particles administered to a subject may be on the order ranging from $10^6$ to $10^{14}$ particles/mL or $10^3$ to $10^{13}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In some embodiments, rAAV particles of higher than $10^{13}$ particles/mL are be administered. In some embodiments, the compositions of rAAV particles administered to a subject may be on the order ranging from $10^6$ to $10^{14}$ vector genomes (vgs)/mL or $10^3$ to $10^{15}$ vgs/mL, or any values there between for either range, such as for example, about $10^6$, $10^7$, $10^8$, $10^9$, $10^{10}$, $10^{11}$, $10^{12}$, $10^{13}$, or $10^{14}$ vgs/mL. In some embodiment, rAAV particles of higher than $10^{13}$ vgs/mL are be administered. The rAAV particles can be administered as a single dose, or divided into two or more administrations as may be required to achieve therapy of the particular disease or disorder being treated. In some embodiments, 0.0001 mL to 10 mLs (for example, or any volumes therebetween) are delivered to a subject.

In some embodiments, a composition described herein may be administered to a subject in need thereof. In some embodiments, the subject is obese. In some embodiments, the subject is overweight. In some embodiments, the subject is diabetic. In some embodiments, the subject is pre-diabetic. In some embodiments, the subject is a subject having a medical need and/or a desire to reduce food intake. In some embodiments, the subject is a mammal. In some embodiments, the subject is a human. In some embodiments, the subject is a pet, a research model, or an agricultural animal. In some embodiments, the subject is a cat, a dog, a mouse, a rat, a horse, a donkey, a cow, a pig, or other animal.

In certain embodiments, a formulation is prepared for spraying into the mouth. The composition may be placed in a container equipped with a sprayer nozzle and either ejected through a pump motion or by release of pressure. In another embodiment, the composition is combined and provided in the form of a chewing gum, lozenge, orally disintegrating tablet, or dissolvable film. In some embodiments, the composition is in a form suitable for injection. In some embodiments, the composition is in a liquid form suitable for topical administration to a subject (e.g., in the mouth, for example on the tongue, under the tongue, on the gums, in the nose, in the throat, etc., or a combination thereof).

The composition may include rAAV particles, polypeptides, and/or nucleic acids, either alone, or in combination with one or more additional active ingredients, which may be obtained from natural or recombinant sources or chemically synthesized.

"Subject", as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans.

"Treating" or "treatment of" as used herein, refers to providing any type of medical or surgical management to a subject. Treating can include, but is not limited to, administering a composition comprising a therapeutic agent to a subject. "Treating" includes any administration or application of an agent or composition of the invention to a subject for purposes such as curing, reversing, alleviating, reducing the severity of, inhibiting the progression of, or reducing the likelihood of a disease, disorder, or condition or one or more symptoms or manifestations of a disease, disorder or condition. In a specific example, a composition of this invention can be administered to a subject who has developed or is at risk of developing pre-diabetes, diabetes, is overweight, is obese, or other ailments related to being overweight or having to do with diabetes (e.g., diabetic retinopathy). A composition of this invention can be administered prophylactically, i.e., before development of any symptom or manifestation of the condition. Typically in this case the subject will be at risk of developing the condition. Treating also may comprise treating a subject exhibiting symptoms of a certain disease or condition. A therapeutically acceptable amount may be an amount that is capable of treating a disease, e.g., diabetes.

As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

PYY Gene Therapy

Peptide YY (PYY) is a satiation gut peptide secreted from the neuro-endocrine L cells from the small intestine and colon epithelia. PYY is secreted into the blood stream and subsequently activates Y receptors in the arcuate nucleus of the hypothalamus thus inducing satiation. In addition to the plasma, PYY has also been detected in saliva in naive, untreated mice, while at the same time identifying the respective Y2 receptor in the tongue epithelia. It has been hypothesized that: long-term expression of genes coding for satiation peptide in salivary gland will reduce food intake and body weight in obese animals.

In order to overexpress PYY, a rAAV vector was constructed harboring the pre-pro-Peptide YY gene (FIG. 1). rAAV-PYY was administered into the salivary glands through the salivary ducts. Injection of rAAV-PYY resulted in a long-term (up to 6 months) expression of Peptide YY as measured by the respective ELISA assay (not shown).

Figure 2:
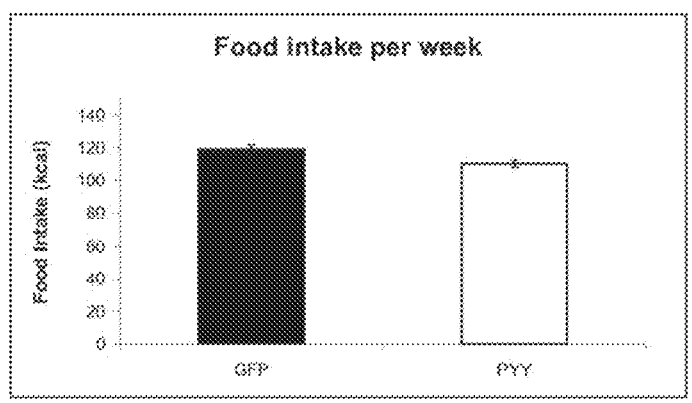
FIG. 2 depicts food intake per week in 8 month-old DIO mice injected with rAAV-PYY vs. rAAV-GFP. *P<0.05.
Figure 3:
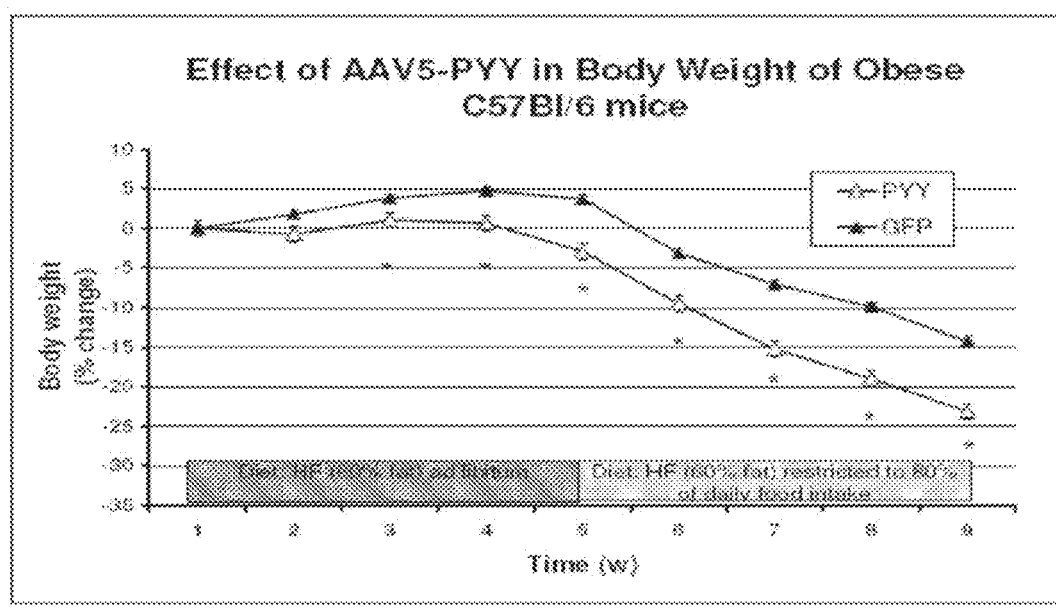
FIG. 3 depicts body weight change in 8 month-old diet-induced obese (DIO)-mice injected with rAAV-PYY vs. rAAV-GFP (controls). *P<0.05.

The ectopic expression of PYY transgene in lean as well as in diet-induced obese mice produced a significant decrease in food intake and body weight compared to control group injected with reporter vector rAAV-GFP (FIGS. 2 and 3). The results demonstrated that long-term expression of peptide YY transgene delivered by a viral vector is a viable therapy for the treatment of obesity.

In some embodiments, food intake will be significantly reduced by long term expression of both PYY and a GLP-1 or analog thereof (e.g., Ex-4), for example using an rAAV vector that expresses both polypeptides (e.g., in similar amounts, or in different amounts).

Example 2

Long-Term Peptide YY Gene Therapy: Addressing Existing Controversy

Peptide YY (PYY) is a satiation gut hormone released postprandially mainly by the gut. The effects of acute and chronic administration of PYY are controversial. Several groups have found a significant decrease in food intake (FI) and body weight (BW) in animal experiments and in human trials, while other groups have been unable to reproduce this data. The controversy can be related to several behavioral factors including acclimatization and stress, as well as varying experimental conditions. To eliminate these factors and to address the effect of long-term overexpression of PYY developed animal models, C57BL/6 mice, with either homotopic or ectopic expression of pre-pro-PYY transgene delivered by a single injection of a viral vector. For the enhanced homotopic expression, the vector was delivered through superior mesenteric artery (SMA) to target the colon and small intestine where PYY is normally produced. For the ectopic expression, the vector had been delivered either into the $3^{rd}$ ventricle in the brain targeting hypothalamus, or into the salivary ducts to target submandibular salivary glands to induce PYY secretion in to saliva. All treated mice were fed a high fat diet (60% fat) ad libitum, FI and BW were measured once a week for 30 weeks. In SMA-injected mice, we documented a sustained two-fold increase of PYY in plasma during fasting and ten-fold increase one hour after feeding. In spite of the significant increase of systemic PYY, no differences in BW or FI were documented at 30 weeks post-injection. On the contrary, in mice with PYY-encoding vector injected either centrally or in the salivary glands, the concentration of plasma PYY remained unchanged. Thus, PYY produced by salivary glands or applied topically to the mouth do not result in systemic increase in PYY, but instead provides therapeutic effect by acting locally. However, centrally-injected mice exhibited significant increase in both BW and FI, while the long-term effect was opposite in salivary gland-treated animals. In satiation behavioral studies, neither treated group show a significant difference in FI after 16, or 24 hrs fasting. The results suggest that the long-term overexpression of PYY has different effects dependent on the targeted site.

Example 3

Administration of Satiation Gut Peptides to Mouth

Satiation gut peptides are secreted into the bloodstream from the small intestine and colon in response to food intake (FI). Their main effect is to induce satiety by activating their specific receptors in the satiety center in the hypothalamus. The most important satiation gut peptides are Peptide YY (PYY), Glucagon-like Peptide 1 (GLP-1), Oxyntomodulin (OXM), and Cholecystokinin (CCK). Acute supplemental therapy with satiation gut peptides reduces FI and body weight (BW) in obese animal models as well as in lean and obese human subjects. Several clinical trials utilizing satiation peptide supplement therapy are currently under way. Unfortunately, the delivery methods of these peptides (iv injections) showed significant side effects and poor adherence. In the pilot study, in addition to the plasma, PYY in saliva was also detected in naive, untreated mice, while at the same time identifying the respective Y2 receptor in the tongue epithelia. Based on these novel findings, the inventors have developed a non-invasive, easy-to-use mouth spray to deliver these peptides. The aim is to reduce voluntary FI by inducing an early satiation effect mediated by an increased concentration of these peptides in the saliva. Incremental reduction in FI over the prolonged period of time will result in reduced BW and improved health.

Materials and Methods:

Synthetic PYY was purchased from Bachem, Inc USA (Cat #H-6042) and diluted in sterile $H_2O$. Sterile un-used perfume sample vials (Saphora) were utilized to administer PYY in the form of a mouth spray. It was estimated that the volume of one spray approximates to about 25 l.

Mice were conditioned three times to 24 hours fasting starting at the beginning of the dark cycle and ending at the end of the light cycle. At the end of the fasting cycle and as a part of conditioned routine, a sterile water spray had been administered into the mouth. All the experiments were done during the first hour of the dark cycle after fasting. Once the dark cycle started, mice were sprayed once with either PYY or sterile $H_2O$ in a total volume of 25 l per spray. After the treatment, mice were returned to their cages and ten minutes later pre-weighted chow was provided. One hour later, the amount of consumed chow had been recorded by measuring the leftover amount. When the experiments were repeated, mice were fasted only once a week with the control and experimental groups rotated.

Figure 4A:
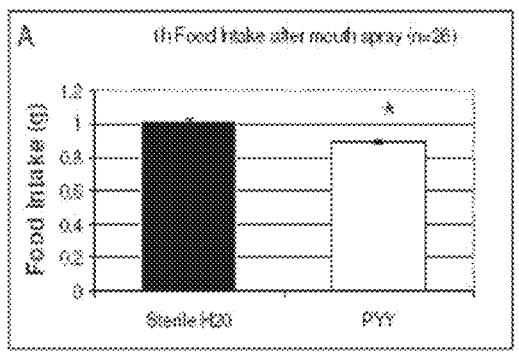
FIGS. 4A-4D depict the effects of Peptide YY Mouth Spray.
Figure 4B:
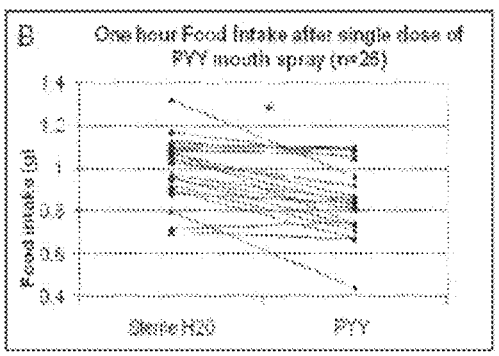
Figure 4C:
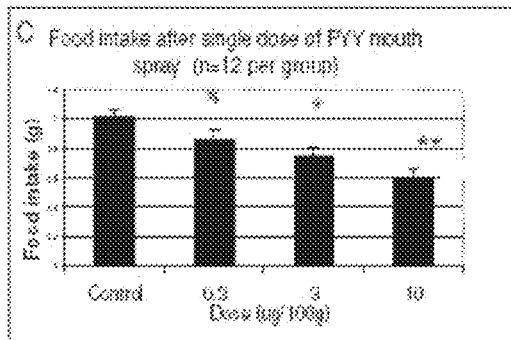
Figure 4D:
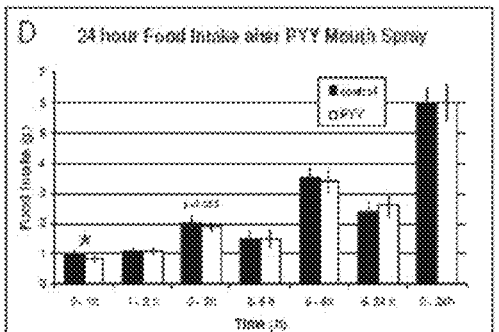

Mice sprayed with PYY consumed significantly (P=0.03) less food (15% on average) compared to the control group sprayed with $H_2O$ (FIGS. 4A, 4B). A significant PYY dose response effect to FI (FIG. 4C) was also documented. After PYY mouth spray, there was a pronounced early satiety effect followed by compensatory higher food intake resulting in similar overall 24 hr period FI for both experimental and control groups (FIG. 4D). This data correlates with previously published observation showing no difference in FI during 24 hours after IP or IV injections. This data, however, reflect the ad libitum pattern of food consumption in mice. In humans, with a defined pattern of three meals per day, with PYY spray application prior to each meal, the treatment is anticipated to reduce overall FI over a 24 hour period.

Accordingly, the increase in PYY concentration delivered by mouth spray has a potential to be utilized as a treatment for obesity by reducing voluntary FI.

Similar techniques will be used for delivering PYY and GLP-1 or an analog thereof to a subject to produce synergistic decreases in food intake and/or more significant weight loss in the subject.

Example 4

Long-Term Salivary PYY3-36 Treatment Modulates Aggressive Behavior

The NPY pathway modulates food intake, body weight, energy expenditure, blood pressure, cortical excitability, circadian rhythms, stress response, emotions, memory, attention, learning, aggression, ethanol susceptibility and pain processing. The NPY pathway has also been related to the mechanism of epilepsy, neurogenesis, neuroprotection, analgesia, anxiety and depression (1, 2). The widespread effects of NPY are mediated by G-protein coupled receptors Y1, Y2, Y4, Y5 and Y6.

Components of the Neuropeptide Y (NPY) expressed widely in the CNS have been linked to aggression, anxiety and depression. For example, NPY Y1 and Y4 receptor knockout mice exhibit abnormally aggressive behavior (1). Furthermore, both pharmacological inhibition of NPY Y2 receptor and NPY Y2 receptor knockout show an anxiolytic, antidepressant phenotypes with reduced attention and increased impulsivity (3, 4)'(5). However, so far little is known about the role of NPY Y2 receptors in aggressive behavior.

NPY Y2 receptors endogenous agonist is $PYY_{3-36}$. Recently, it was reported that augmentation of salivary $PYY_{3-36}$ modifies feeding behavior in mice. The long-term increase of salivary $PYY_{3-36}$ by using a recombinant Adeno-associated virus (rAAV-PYY), produced a significant decrease in body weight and food intake in obese mice. Unexpectedly, in addition to modulating the feeding behavior, the long term over-expression of salivary $PYY_{3-36}$ also appears to modulate aggressive behavior.

Data presented in this report indicate that long-term expression of Peptide $YY_{3-36}$, an agonist of NPY Y receptors with higher affinity for the Y2 receptor, abolish aggressive behavior in mice. To test these observations, we used the territorial Resident/Intruder (R/I) aggressive paradigm (6), a standard test for evaluating rodent aggressive behavior. The test was applied on three different occasions using different intruders. Tests were recorded and analyzed in a blind manner using the Observer v5.0 software (Noldus Information Technology (7).

Figure 5A:
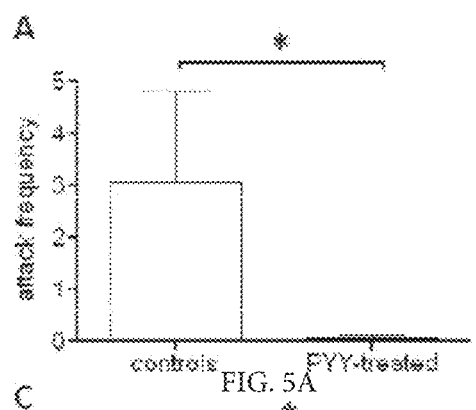
FIGS. 5A-5D relate to the effects of extended PYY administration on behavior of mice concerning (FIG. 5A) attack frequency (FIG. 5B) threat frequency (FIG. 5C) chase frequency and (FIG. 5D) frequency.
Figure 5B:
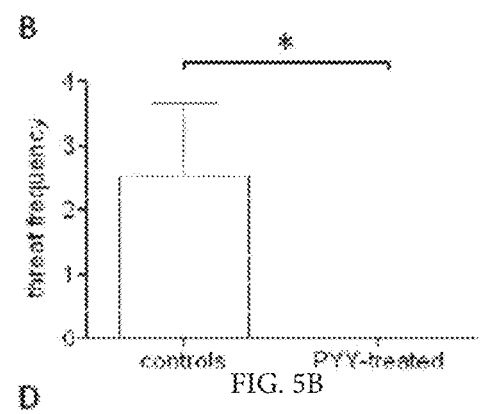
Figure 5C:
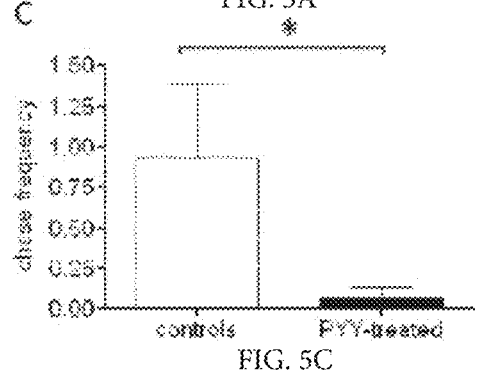
Figure 5D:
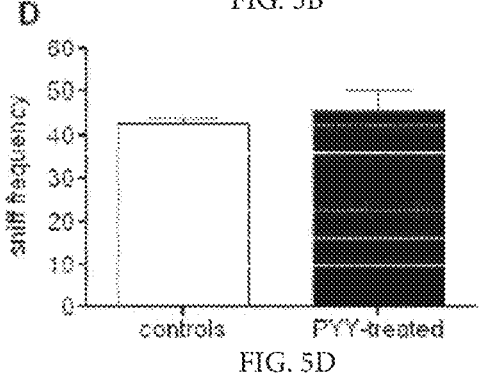
Figure 6:
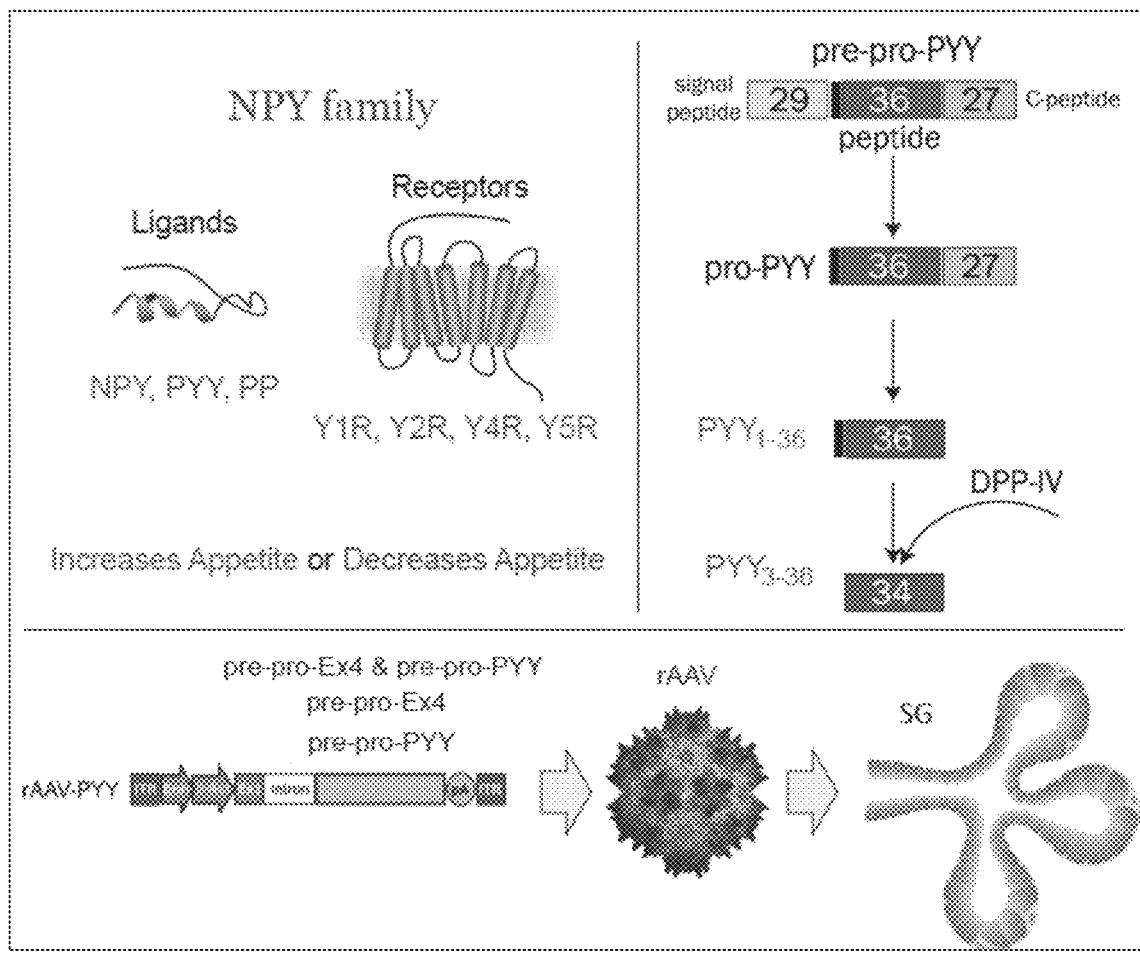
FIG. 6 depicts the NPY family, distinguishing between ligands and receptors that increase or decrease appetite, as well as pre-pro-PYY, and truncated forms that may then be delivered to salivary glands using viral vector-mediated gene delivery.

The aggressive behavior was analyzed by the frequency, duration and latency of attacks, threats and chase from the resident to the intruder mice. $PYY_{3-36}$ treated mice displayed a 44-fold decrease in the number of attack events compare to controls [$PYY_{3-36}$ 0.07.+−.0.067 events per 10 min, vs. Controls 3.07.+−.1.74 events in 10 min, n=5, p<0.05] (FIG. 5A). Likewise, $PYY_{3-36}$ treated mice had a significant decrease in attack duration and a significant increase in attack latency. Similarly, $PYY_{3-36}$ treated mice had a significant decrease in threat events and duration compare to controls (FIG. 5B) and a decrease in chase events and duration compare to control mice (FIG. 5C). Interestingly, even though an aggressive behavior was almost completely abrogated, the normal social interactions manifested by sniffing did not change (FIG. 5D).

These dramatic changes in territorial aggression suggest that the long-term treatment with NPY Y2 receptors agonists such as $PYY_{3-36}$ modulates both feeding and aggressive behaviors. Because $PYY_{3-36}$ has recently been tested in clinical trials for weight loss in obese adult subjects, the unintended while favorable effects shown here must be taken in consideration before such agonists are approved for the long-term treatment of obesity. This is especially important in light of the Y receptors cross talk and interactions as shown in genetically modified mice models (8). Further studies are needed to understand the long-term effect of Y receptors agonists in feeding and aggressive behavior, as well as in depression and anxiety.

Materials and Methods:

Vector design: A recombinant adeno-associated virus encoding murine pre-pro-PYY (rAAV-PYY) under the control of a strong constitutive CMV/-actin promoter and the control rAAV-GFP were pseudotyped into rAAV serotype 5 capsids as having higher transduction in salivary glands (SG) (9). The production, purification and titration of the viral vectors were performed as described previously (10).

Mouse studies: This study was approved by the Animals Care and Use Committee of The National Institute of Dental and Craniofacial research and by the Biosafety Committee of the National Institute of Health (Bethesda, Md.). All mice procedures were done in accordance with the principles of the National Research Council's guide for the Care and Use of Laboratory Animals. Studies were done in male Balb/c (Harlan Sprague Dawley, Walkersville, Md.) mice housed at 22-24° C. in a 12 hours light/dark cycle (lights off at 1800). Forty five days old male Balb/C mice (n=5) were administered a single dose of (100 l, $10^{10}$ vector genomes) rAAV-PYY, rAAV-GFP or saline control bi-laterally into the orifice of the submandibular salivary gland as described by Katano et al (9).

Metabolic profile: Mice had free access to water and food (normal chow). Food intake and body weight were measured weekly for 24 weeks.

Behavioral studies: Aggression territorial-Intruder test were performed on week 24 after the treatment (6). Briefly, PYY-, or GFP-treated resident mice were individually housed for at least two weeks prior to testing. Bedding from cages was not changed during the testing period to avoid unnecessary stress. On the day of the experiment, a smaller size intruder was placed into the resident cage for 10 minutes and the resident's behavior was recorded with a video camera. Each experiment was repeated 3 times on three different occasions and with different intruders. The videos from the experiments were analyzed for non-aggressive and aggressive behavior by an expert in a blind manner using The Observer v5.0 software (Noldus Information Technology) (7).

Statistical analysis: Statistical analysis was conducted using un-paired Student's t-test or by a Mann-Whitney test with significance at P<0.05. Data was reported in mean.+−.SEM.

Metabolic Profile: rAAV-PYY treated mice weekly caloric intake was significantly lower than rAAV-GFP control mice (rAAV-PYY 95.53.+−.2.35 kcal vs. rAAV-GFP 107.44.+−.3.22 kcal, p<0.002). Twenty two weeks after vector delivery, the rAAV-PYY treated mice gained significantly less weight than the controls mice (rAAV-PYY 5.33.+−.0.63 g vs. rAAV-GFP 6.28.+−.0.68 g, p<0.05). These data suggest that long-term chronic elevation of $PYY_{3-36}$ in saliva of lean mice modulates feeding behavior by decreasing food intake and body weight.

REFERENCES CITED FOR EXAMPLE 4

1. T. Karl, H. Herzog, Peptides 28, 326 (February 2007).
2. E. E. Benarroch, Neurology 72, 1016 (Mar. 17, 2009, 2009).
3. A. Tschenett et al., Eur J Neurosci 18, 143 (July 2003).
4. J. P. Redrobe, Y. Dumont, H. Herzog, R. Quirion, Behav Brain Res 141, 251 (May 15, 2003).
5. B. Greco, M. Carli, Behav Brain Res 169, 325 (May 15, 2006).
6. T. Karl et al., Proc Natl Acad Sci USA 101, 12742 (Aug. 24, 2004).
7. A. M. Muehlmann, B. D. Brown, D. P. Devine, J Pharmacol Exp Ther 324, 214 (Jan. 1, 2008, 2008).
8. W. Wittmann, S. Loacker, I. Kapeller, H. Herzog, C. Schwarzer, Neuroscience 136, 241 (2005).
9. H. Katano et al., Gene Ther 13, 594 (April 2006).
10. S. Zolotukhin et al., Methods 28, 158 (October 2002).

Example 5

Expression of PYY and Exendin-4 in Murine Saliva Promotes Weight Loss

PYY and GLP-1 are both produced in pancreatic L-cells and secreted simultaneously into the blood stream in response to nutrient uptake. Recently a novel role of salivary PYY in the modulation of weight loss and food intake in mice was demonstrated. Similarly, a decrease in food intake of mice given Exendin-4 (Ex-4), a GLP-1 analog, in the form of an oral spray prior to meals was observed. Both of these peptides individually modulate body weight, we have evidence that, when used in combination, PYY and Ex-4 may have a synergistic effect on modulation of body weight.

Figure 7A:
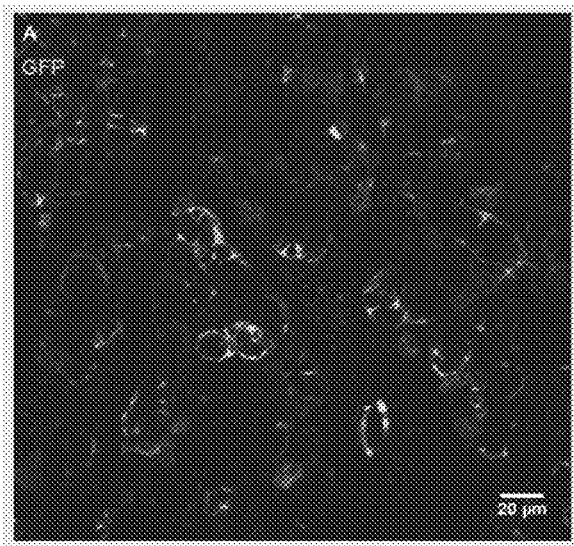
FIGS. 7A-7B show transduction of murine submandibular salivary gland and liver via AAV8 administration to the murine salivary glands via ductile cannulation.
Figure 7B:
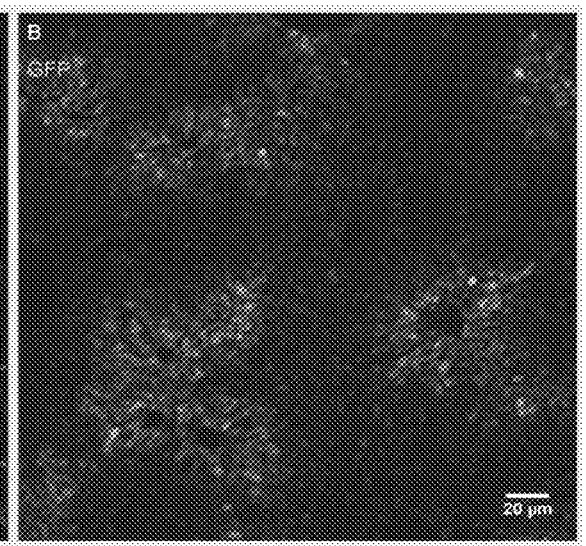

Using recombinant Adeno-associated viral vector serotype 8 (rAAV8) expressing GFP, Ex-4, PYY or both PYY and Ex-4 cDNA, $10^{11}$ viral genomes of vector were administered to the submandibular salivary glands of mice. The body weight of mice was observed over a 10 week period during which mice were transition from normal chow to a high fat (HF) diet. Mice given both Ex-4 and dual PYY Ex-4 AAV8 vectors demonstrated a significant decrease in body weight when compared to GFP control mice. Although PYY AAV8 mice demonstrated a decreasing weight loss trend over the course of the experiment, their weight loss was not significant when compared with GFP demonstrated rapid, significant weight loss one week after vector administration, demonstrating the increased efficacy of this combined therapeutic approach. FIGS. 7A-7B show transduction of murine submandibular salivary gland and liver via AAV8 administration to the murine salivary glands via ductile cannulation. FIG. 7 shows confocal microscopy imaging of eGFP expression in WT C57BL/6 mouse 2 weeks after AAV8-GFPsc administration via salivary gland ductile cannulation. FIG. 7A shows eGFP expression in fixed frozen mouse submandibular gland sections, and FIG. 7B shows fixed frozen liver sections.

Figures 8A, 8B:
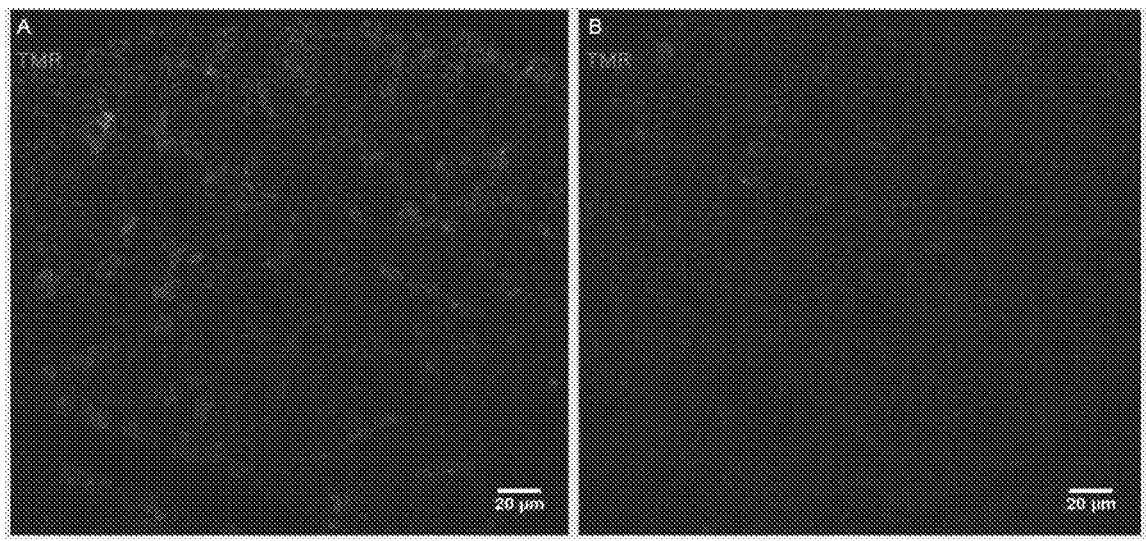
FIGS. 8A-8B shows immunofluorescent staining of mouse submandibular salivary gland in AAV8-GFP-EX4sc injected mice (FIG. 8A) and WT non-injected mice (FIG. 8B). Fixed frozen tissue sections stained with a biotinylated mAb against Exendin-4 then detected by streptavidin-HRP and tyramide-TMR flurophore.
Figure 9:
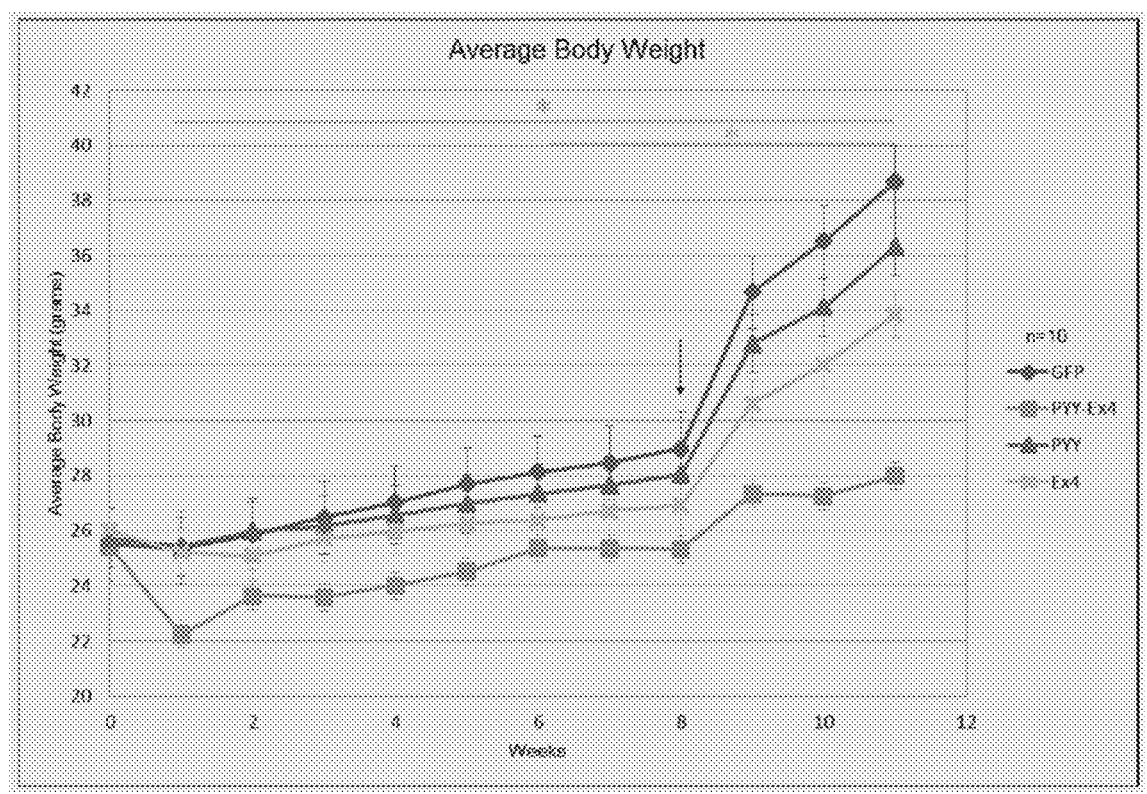
FIG. 9 depicts the average body weight over an 11 week period of mice injected with AAV8-GFPsc (diamonds), AAV8-GFP-Ex4 (X's), AAV8-jPYYsc (triangles), or AAV8-PYY-Ex4sc (squares). Mice switched to a high fat diet week 8 indicated by black arrow. Significance was calculated by two-tailed unpaired t-test with significance threshold of p<0.05. Significance is indicated by *.

Immunofluorescent staining of the submandibular salivary gland and liver of AAV8-GFP-Ex-4sc injected mice confirmed the presence of the Ex-4 protein in the submandibular salivary gland (FIG. 8A). Immunofluorescent staining of wild type submandibular salivary glands was overall negative with a few localized points of nonspecific immunoreactivity (FIG. 8B). This non-specific immunofluorescence (FIG. 8B) may be eliminated by increasing the tissue blocking period or decreasing the concentration of primary anti-Ex-4 antibody. FIG. 9 depicts the average body weight over an 11 week period of mice injected with AAV8-GFPsc (diamonds), AAV8-GFP-Ex4 (X's), AAV8-jPYYsc (triangles), or AAV8-PYY-Ex4sc (squares). Mice switched to a high fat diet week 8 indicated by black arrow. Significance was calculated by two-tailed unpaired t-test with significance threshold of p<0.05. Significance is indicated by *.

Accordingly, there is an increased effect on body weight reduction when both PYY and Ex-4 expression are increased as opposed to PYY or Ex-4 alone. AAV8 transduces the murine salivary gland, but also transduces the liver even when applied directly to the salivary glands via ductile cannulation. This may potentially be avoided by targeting specific cell types, such as epithelial cells versus neurons, depending upon what receptors are present and which peptide is being used.

Example 6

PYY and EX-4 Gene Therapy

Peptide tyrosine tyrosine (PYY) and glucagon-like peptide 1 (GLP-1) are gastrointestinal peptides secreted into the circulation in response to nutrient uptake. Both circulating PYY and GLP-1 have been shown to suppress food intake and promote weight loss in mice. Recently, a putative role for salivary PYY has been discovered, which is the reduction of food intake and body weight of mice without inducing conditioned taste aversion (CTA), which is an indication of nausea. See M. D. Hurtado, et al., Salivary peptide tyrosine-tyrosine 3-36 modulates ingestive behavior without inducing taste aversion. *J. Neurosci.* 33, 18368-18380 (2013). Salivary GLP-1 has also been implicated in satiation as its cognate receptor, GLP-1 receptor, has been shown to be expressed on taste bud associated nerve fibers. See B. Martin et al., Modulation of taste sensitivity by GLP-1 signaling in taste buds. *Ann NY Acad Sci*, 1170, 98-101 (2009). Although PYY and GLP-1 have been studied individually as obesity therapies, the effects of these peptides on weight loss and food intake when administered together, particularly in the saliva, is not known.

The present study reports on the use of recombinant Adeno-associated viral vectors (rAAV) to deliver PYY and Exendin-4 transgenes to the submandibular salivary glands of mice simultaneously, and produced a marked increase in weight loss in mice given dual PYY and Exendin vectors compared to single transgene containing vectors. Ex-4 is a GLP-1 analog resistant to proteolytic degradation, and therefore was selected for expression over GLP-1.

In order to determine whether the observed anorexigenic effect of PYY and Ex-4 is modulated through taste perception, a Davis Rug gustometer was utilized to generate brief access taste response curves for a panel of tastants for all groups of treated mice. The Ex-4 group as well as the PYY-Ex4 dual group displayed a significant increase in sensitivity to intralipid stimulus, indicating that this taste modality plays a role in BW modulation. The observed weight loss and altered taste perception was complicated by the unintended transduction of hepatocytes. Unintended transduction of the liver may result in elevated levels of PYY and Ex-4 in the bloodstream in addition to saliva. In order to distinguish between the saliva-specific effect of the dual PYY-Ex-4 vector administration, a viral construct was developed containing miR122 target sequences, a liver specific micro RNA (miRNA), and miR206, a skeletal muscle specific miRNA, target sequences in the 3' UTR of each construct. These micro RNA target sequences suppress vector expression in off-target tissues, such as skeletal muscle and liver. Additionally, all viral constructs were packaged into AAV5, which has the same transduction efficiency of salivary glands, but decreased transduction of the murine liver. Using these miRNA constructs, no detectable expression of GFP in the murine liver was observed, allowing for tissue or cell specific therapy.

The present application also comprises inducing satiety using peptides that target specific receptors in different cell types. For example, targeting the PYY-preferring receptor, Y2R, which may be found in murine tongue epithelial cells, but not in taste cells. See Acosta, A. et al., Salivary PYY: A Putative Bypass to Satiety. PLoS ONE 6(10): (October 2011). Significant levels of expression of Y2R mRNA by RT-PCT using mRNA isolated from murine tongue epithelia have been detected. Acosta, A. et al., Salivary PYY: A Putative Bypass to Satiety, PLoS ONE 6(10) (October 2011). In wt C57l/6 mice, one layer of basal epithelial cells was also strongly positive for Y2R receptors, and epithelial cells lining up ducts of the von Ebner's gland (VEG) expressed Y2R as well. Id. No Y2R was detected in taste cells. Id. Y2R expression has also been detected in a single apical layer of progenitor cells in the tongue epithelium, as well as in von Ebner's gland ducts and acini, suggesting a possible trophic role of PYY signaling in mitotic signaling/regeneration. Id. The apical layer of Y2R-positive cells appears to be innervated with neuron filaments. Thus, the anatomical location of Y2R-positive cells, combined with their somatosensory innervation indicates a potential functional role for salivary PYY ligand and its preferred Y2 receptor related to the regulation of feeding behavior. Id. PYY, like other peptides, is potentially vulnerable to breakdown by enzymes in saliva or acids in the digestive system upon oral delivery. However, topically applied PYY can induce satiety without raising plasma levels, but duration of therapeutic effect varies. The ability to effect local delivery and Y2R selective agonist data make the oral mucosal epithelial Y2R-positive cells targets for anorexic actions of salivary PYY, and indicates the existences of a putative neuronal circuit initiated in the oral cavity. Id. Thus, the present application includes targeted delivery of rAAV serotypes expressing PYY, or targeted topical delivery of the peptide itself to the mouth or specific tissues within the mouth. Comparable cell-specific targeted therapy using vectors or topically applied peptides are also contemplated by aspects of the application.

In some embodiments, sustained elevation of PYY and Exendin-4 (EX-4, a GLP-1R agonist) in saliva of mice results in an anorexigenic effect. Using rAAV serotype 8 (rAAV8), gene transfer of GFP (control), PYY, EX-4 and PYY-EX-4 dual vectors was performed into the submandibular salivary glands of C57BL/6 mice fed a high fat diet. A significant decrease in body weight (BW) of mice treated with either Ex-4 or PYY-Ex4 dual vectors was observed, in comparison to controls. Mice treated with PYY-Ex-4 dual vector displayed a significant decrease in BW as early as 1 week post vector administration, whereas mice treated with Ex-4 alone did not demonstrate a significant loss until 8 weeks post-injection. PYY mice, while demonstrating a decreasing trend in BW gain compared to GFP mice, did not show a significant difference BW during the 12-week experiment. Treatments using the combination of PYY and Ex-4, either by gene expression, or by administration of a combination of PYY and Ex-4 via topical administration, spray, oral formulations (sprays, lozenges, dissolvable films, orally disintegrating tablets, buccal dosage forms and the like) do not detectably increase plasma levels of PYY or Ex-4. Other embodiments of the present invention comprise one or more of AAV serotypes 1-10 or other AAV serotypes for use in the present compositions and methods.

Non-Limiting Sequences

Human Peptide YY amino acid sequence (SEQ ID NO: 1):

Met Val Phe Val Arg Arg Pro Trp Pro Ala Leu Thr

Thr Val Leu Leu Ala Leu Leu Val Cys Leu Gly Ala

Leu Val Asp Ala Tyr Pro Ile Lys Pro Glu Ala Pro

Gly Glu Asp Ala Ser Pro Glu Glu Leu Asn Arg Tyr

Tyr Ala Ser Leu Arg His Tyr Leu Asn Leu Val Thr

Arg Gln Arg Tyr Gly Lys Arg Asp Gly Pro Asp Thr

Leu Leu Ser Lys Thr Phe Phe Pro Asp Gly Glu Asp

Arg Pro Val Arg Ser Arg Ser Glu Gly Pro Asp Leu

Trp

Human Peptide YY 3-36 amino acid sequence (SEQ ID NO: 2):

Ile Lys Pro Glu Ala Pro Gly Glu Asp Ala Ser Pro

Glu Glu Leu Asn Arg Tyr Tyr Ala Ser Leu Arg His

Tyr Leu Asn Leu Val Thr Arg Gln Arg Tyr

Other examples of PYY sequences can be found in the following references, the entire contents of which are included herein: Tatemoto K, Nakano I, Makk G, Angwin P, Mann M, Schilling J, Go V L. Isolation and primary structure of human peptide YY. Biochem Biophys Res Commun. 1988 Dec. 15; 157(2):713-7; Eberlein G A, Eysselein V E, Schaeffer M, Layer P, Grandt D, Goebell H, Niebel W, Davis M, Lee T D, Shively J E, et al. A new molecular form of PYY: structural characterization of human PYY(3-36) and PYY(1-36). Peptides. 1989 July-August; 10(4):797-803; and Kohri K, Nata K, Yonekura H, Nagai A, Konno K, Okamoto H. Cloning and structural determination of human peptide YY cDNA and gene. Biochim Biophys Acta. 1993 Jun. 25; 1173(3):345-9 (discloses nucleotide sequence, SEQ ID NO: 2).

Oxyntomodulin (human, SEQ ID NO: 3):

His Ser Gln Gly Thr Phe Thr Ser Asp Tyr Ser Lys

Tyr Leu Asp Ser Arg Arg Ala Gln Asp Phe Val Gln

Trp Leu Met Asn Thr Lys Arg Asn Lys Asn Asn Ile

Ala

Other examples of oxyntomodulin sequences can be found in PCT applications WO/2007/100535 and WO/2005/035761, there entire contents of which are incorporated by reference herein.

Cholecystokinin (*Homo sapiens* (SEQ ID NO: 4)):

Met Asn Ser Gly Val Cys Leu Cys Val Leu Met Ala

Val Leu Ala Ala Gly Ala Leu Thr Gln Pro Val Pro

Pro Ala Asp Pro Ala Gly Ser Gly Leu Gln Arg Ala

Glu Glu Ala Pro Arg Arg Gln Leu Arg Val Ser Gln

Arg Thr Asp Gly Glu Ser Arg Ala His Leu Gly Ala

Leu Leu Ala Arg Tyr Ile Gln Gln Ala Arg Lys Ala

Pro Ser Gly Arg Met Ser Ile Val Asn Leu Gln Asn

Leu Asp Pro Ser His Arg Ile Ser Asp Arg Asp Tyr

Met Gly Trp Met Asp Phe Gly Arg Arg Ser Ala Glu

Glu Tyr Glu Tyr Pro Ser

*Homo sapiens*-full cDNA (SEQ ID NO: 5):

| | | | | | | |
|---|---|---|---|---|---|---|
| cacttcaacc | ggttgtcgcc | ccagtggccg | ccctctgagc | acgtgttact | gccagtctgc | 60 |
| gtcagcgttg | ggtaaataca | tgactggccg | acgccgccgg | gcggggctat | ttaagagaca | 120 |
| gccgcccgct | ggtcctccct | gaacttggct | cagctgccgg | gctgctccgg | ttggaaacgc | 180 |
| caagccagct | gcgtcctaat | ccaaaagcca | tgaacagcgg | cgtgtgcctg | tgcgtgctga | 240 |
| tggcggtact | ggcggctggc | gccctgacgc | agccggtgcc | tcccgcagat | cccgcgggct | 300 |
| ccgggctgca | gcgggcagag | gaggcgcccc | gtaggcagct | gagggtatcg | cagagaacgg | 360 |

```
atggcgagtc ccgagcgcac ctgggcgccc tgctggcaag atacatccag caggcccgga    420
aagctccttc tggacgaatg tccatcgtta agaacctgca gaacctggac cccagccaca    480
ggataagtga ccgggactac atgggctgga tggattttgg ccgtcgcagt gccgaggagt    540
atgagtaccc ctcctagagg acccagccgc atcagccca  acgggaagca acctcccaac    600
ccagaggagg cagaataaga aaacaatcac actcataact cattgtctgt ggagtttgac    660
attgtatgta tctatttatt aagttctcaa tgtgaaaaat gtgtctgtaa gattgtccag    720
tgcaaccaca cacctcacca gaattgtgca aatggaagac aaaatgtttt cttcatctgt    780
gactcctggt ctgaaaatgt tgttatgcta ttaaagtgat ttcattctga aaaaaaaaa     840 aaaaaaaaa a
``` cDNA encoding SEQ ID NO: 4 (SEQ ID NO: 6):

```
atgaacagcg gcgtgtgcct gtgcgtgctg atggcggtac tggcggctgg cgccctgacg     60
cagccggtgc ctcccgcaga tcccgcgggc tccgggctgc agcgggcaga ggaggcgccc    120
cgtaggcagc tgagggtatc gcagagaacg gatggcgagt cccgagcgca cctgggcgcc    180
ctgctggcaa gatacatcca gcaggcccgg aaagctcctt ctggacgaat gtccatcgtt    240
aagaacctgc agaacctgga ccccagccac aggataagtg accgggacta catgggctgg    300
atggattttg gccgtcgcag tgccgaggag tatgagtacc ctcctag                 348
```

Human Peptide YY 1-36 amino acid sequence (SEQ ID NO: 7):

Tyr Pro Ile Lys Pro Glu Ala Pro Gly Glu Asp Ala
Ser Pro Glu Glu Leu Asn Arg Tyr Tyr Ala Ser Leu
Arg His Tyr Leu Asn Leu Val Thr Arg Gln Arg Tyr

PYY cDNA (SEQ ID NO: 8):

```
gccccctggag gaactgaacc cactatcggt catggggccg agactaaatg tggcgggttg    60
tctttaatct gctgccaaga ggaaactcat tcaggcaagt tcagcccttt atgaggaatt    120
cccctgtggt cacattccaa ttcctggacc tgctgccacc ctcagaactg catgctcctt    180
cttcagactt tctaagaatg actcaggtca ttggtggagt gaagtcaaga tttccaactc    240
agtcacctga agagatggag ataccattca tggagctgga ggtccctgga gatttgggaa    300
ttcagataac aagctaagat aaggagtttg cctacctctg tcctagagcg aagcctgagc    360
cttgggcgcg cagcacacca caagtatctg ttactgtgtt ttgcagaagc ttcaggcggg    420
gatataagcc ccacaaggaa agcgctgagc agaggaggcc tcagcttgac ctgcggcagt    480
gcagcccttg ggacttccct cgccttccac ctcctgctcg tctgcttcac aagctatcgc    540
tatggtgttc gtgcgcaggc cgtggcccgc cttgaccaca gtgcttctgg ccctgctcgt    600
ctgcctaggg gcgctggtcg acgcctaccc catcaaaccc gaggctcccc gcgaagacgc    660
ctcgccggag gagctgaacc gctactacgc ctccctgcgc cactacctca acctggtcac    720
ccggcagcgc tatgggaaaa gagacggccc ggacacgctt ctttccaaaa cgttcttccc    780
cgacggcgag gaccgccccg tcaggtcgcg gtcggagggc ccagacctgt ggtgaggacc    840
cctgaggcct cctgggagat ctgccaacca cgcccacgtc atttgcatac gcactcccga    900
ccccagaaac ccggattctg cctcccgacg gcggcgtctg ggcagggttc gggtgcggcc    960
```

```
ctccgcccgc gtctcggtgc ccccgccccc tgggctggag ggctgtgtgt ggtccttccc   1020
tggtcccaaa ataaagagca aattccacag aaaaaaaaaa aaaaaaaa               1069
```

Human peptide YY amino acid sequence ii (SEQ ID NO: 9):

```
Met Val Phe Val Arg Arg Pro Trp Pro Ala Leu Thr

Thr Val Leu Leu Ala Leu Leu Val Cys Leu Gly Ala

Leu Val Asp Ala Tyr Pro Ile Lys Pro Glu Ala Pro

Arg Glu Asp Ala Ser Pro Glu Glu Leu Asn Arg Tyr

Tyr Ala Ser Leu Arg His Tyr Leu Asn Leu Val Thr

Arg Gln Arg Tyr Gly Lys Arg Asp Gly Pro Asp Thr

Leu Leu Ser Lys Thr Phe Phe Pro Asp Gly Glu Asp

Arg Pro Val Arg Ser Arg Ser Glu Gly Pro Asp Leu

Trp
```

Ex-4 (SEQ ID NO: 10)

```
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser
```

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The teachings of the references cited throughout the specification are incorporated herein in their entirety by this reference to the extent they are not inconsistent with the teachings herein. It should be understood that the examples and the embodiments described herein are for illustrative purposes only and that various modifications or changes in light thereof will be suggested to persons skilled in the art and are to be included within the spirit and purview of this application.

What is claimed is:

1. A method of inducing satiation in a subject comprising administering a recombinant Adeno-associated viral (rAAV) vector comprising an expression cassette that comprises a polynucleotide sequence that encodes a PYY peptide and a Glucagon-like Peptide 1 (GLP-1) analog to the submandibular salivary gland of the subject, wherein the rAAV vector transduces submandibular salivary gland cells, wherein the GLP-1 analog is Exendin-4 (Ex-4) peptide, wherein satiation is observed in the subject more than eight weeks after administration.

2. The method of claim 1 wherein the rAAV vector is in an rAAV particle.

3. The method of claim 1 further comprising administering to the subject oxyntomodulin, cholecystokinin, or a combination thereof.

4. The method of claim 2, wherein said rAAV particle is of serotype 8 or serotype 5.

5. The method of claim 1, wherein said rAAV vector further comprises a polynucleotide sequence that encodes a gut peptide selected from oxyntomodulin, cholecystokinin, or a combination thereof.

6. The method of claim 1, wherein said rAAV vector comprises a dual PYY-Ex-4 vector, wherein the polynucleotide sequence that encodes a PYY peptide and Ex4 peptide is operably connected to a single promoter.

7. The method of claim 1, wherein said rAAV is administered by direct injection, spray, lozenge, topical administration, oral disintegrating tablet, oral dissolvable film or dissolvable planar sheet.

8. The method of claim 5, wherein said rAAV vector comprises a polynucleotide sequence that encodes cholecystokinin.

9. The method of claim 1, wherein said rAAV vector is self-complementary.

10. The method of claim 1, wherein the step of administering provides a reduction in body weight one week after administration relative to an untreated subject.

11. The method of claim 1, wherein the step of administering provides, or continues to provide a reduction in body weight more than eight weeks after administration relative to an untreated subject.

12. The method of claim 1, wherein the concentration of at least one of the PYY peptide and the Ex-4 peptide in the plasma of said subject remains unchanged or decreases.

13. A method of increasing satiation gut peptide concentration in the saliva of a subject, the method comprising administering a rAAV vector comprising an expression cassette that comprises a polynucleotide sequence that encodes a PYY peptide and a Glucagon-like Peptide 1 (GLP-1) analog to the submandibular salivary gland of the subject, wherein the rAAV vector transduces submandibular salivary gland cells, wherein the GLP-1 analog is Exendin-4 (Ex-4) peptide, and wherein an increased satiation gut peptide concentration is observed in the subject more than eight weeks after administration.

14. The method of claim 13, wherein the concentration of at least one of the PYY peptide and the Ex-4 peptide in the plasma of said subject remains unchanged or decreases.

15. The method of claim 13, wherein the step of administering provides a reduction in body weight one week after administration relative to an untreated subject.

16. The method of claim 13, wherein the step of administering provides, or continues to provide a reduction in body weight more than eight weeks after administration relative to an untreated subject.

17. The method of claim 13, wherein the rAAV vector is in an rAAV particle.

18. The method of claim 13, wherein said rAAV vector is self-complementary.

\* \* \* \* \*

SEQUENCE LISTING

```
<160> NUMBER OF SEQ ID NOS: 10

<210> SEQ ID NO 1
<211> LENGTH: 97
<212> TYPE: PRT
<213> ORGANISM: Homo sapiens

<400> SEQUENCE: 1

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Gly Glu Asp Ala Ser Pro Glu Glu Leu Asn Arg Tyr
        35                  40                  45

Tyr Ala Ser Leu Arg His Tyr Leu Asn Leu Val Thr Arg Gln Arg Tyr
    50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp

<210> SEQ ID NO 2
<211> LENGTH: 34
<212> TYPE: PRT
<213> ORGANISM: Homo sapiens

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 3
<211> LENGTH: 37
<212> TYPE: PRT
<213> ORGANISM: Homo sapiens
```

<400> SEQUENCE: 3

His Ser Gln Gly Thr Phe Thr Ser Asp Tyr Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 4
<211> LENGTH: 115
<212> TYPE: PRT
<213> ORGANISM: Homo sapiens

<400> SEQUENCE: 4

Met Asn Ser Gly Val Cys Leu Cys Val Leu Met Ala Val Leu Ala Ala
1               5                   10                  15

Gly Ala Leu Thr Gln Pro Val Pro Pro Ala Asp Pro Ala Gly Ser Gly
            20                  25                  30

Leu Gln Arg Ala Glu Glu Ala Pro Arg Arg Gln Leu Arg Val Ser Gln
        35                  40                  45

Arg Thr Asp Gly Glu Ser Arg Ala His Leu Gly Ala Leu Leu Ala Arg
    50                  55                  60

Tyr Ile Gln Gln Ala Arg Lys Ala Pro Ser Gly Arg Met Ser Ile Val
65                  70                  75                  80

Lys Asn Leu Gln Asn Leu Asp Pro Ser His Arg Ile Ser Asp Arg Asp
                85                  90                  95

Tyr Met Gly Trp Met Asp Phe Gly Arg Arg Ser Ala Glu Glu Tyr Glu
            100                 105                 110

Tyr Pro Ser
        115

<210> SEQ ID NO 5
<211> LENGTH: 851
<212> TYPE: DNA
<213> ORGANISM: Artificial Sequence
<220> FEATURE:
<223> OTHER INFORMATION: Synthetic polynucleotide

<400> SEQUENCE: 5
cacttcaacc ggttgtcgcc ccagtggccg ccctctgagc acgtgttact gccagtctgc      60
gtcagcgttg gtaaatacat tgactggccg acgccgccgg gcggggctat ttaagagaca     120
gccgcccgct ggtcctccct gaacttggct cagctgccgg gctgctccgg ttggaaacgc     180
caagccagct gcgtcctaat ccaaaagcca tgaacagcgg cgtgtgcctg tgcgtgctga     240
tggcggtact ggcggctggc gccctgacgc agccggtgcc tcccgcagat cccgcgggct     300
ccgggctgca gcgggcagag gaggcgcccc gtaggcagct gagggtatcg cagagaacgg     360
atggcgagtc ccgagcgcac ctgggcgccc tgctggcaag atacatccag caggcccgga     420
aagctccttc tggacgaatg tccatcgtta agaacctgca gaacctggac cccagccaca     480
ggataagtga ccgggactac atgggctgga tggattttgg ccgtcgcagt gccgaggagt     540
atgagtaccc ctcctagagg acccagccgc catcagccca acgggaagca acctcccaac     600
ccagaggagg cagaataaga aaacaatcac actcataact cattgtctgt ggagtttgac     660
attgtatgta tctatttatt aagttctcaa tgtgaaaaat gtgtctgtaa gattgtccag     720
tgcaaccaca cacctcacca gaattgtgca aatggaagac aaaatgtttt cttcatctgt     780

```
gactcctggt ctgaaaatgt tgttatgcta ttaaagtgat tcattctga aaaaaaaaaa      840 aaaaaaaaaa a                                                          851

<210> SEQ ID NO 6
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 6
atgaacagcg gcgtgtgcct gtgcgtgctg atggcggtac tggcggctgg cgccctgacg       60
cagccggtgc ctcccgcaga tcccgcgggc tccgggctgc agcgggcaga ggaggcgccc      120
cgtaggcagc tgagggtatc gcagagaacg atggcgagt cccgagcgca cctgggcgcc      180
ctgctggcaa gatacatcca gcaggcccgg aaagctcctt ctggacgaat gtccatcgtt      240
aagaacctgc agaacctgga ccccagccac aggataagtg accgggacta catgggctgg      300
atggattttg ccgtcgcag tgccgaggag tatgagtacc cctcctag                   348

<210> SEQ ID NO 7
<211> LENGTH: 36
<212> TYPE: PRT
<213> ORGANISM: Homo sapiens

<400> SEQUENCE: 7

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 8
<211> LENGTH: 1069
<212> TYPE: DNA
<213> ORGANISM: Artificial Sequence
<220> FEATURE:
<223> OTHER INFORMATION: Synthetic polynucleotide

<400> SEQUENCE: 8
gcccctggag gaactgaacc cactatcggt catggggccg agactaaatg tggcgggttg       60
tctttaatct gctgccaaga ggaaactcat tcaggcaagt tcagcccttt atgaggaatt      120
cccctgtggt cacattccaa ttcctggacc tgctgccacc ctcagaactg catgctcctt      180
cttcagactt tctaagaatg actcaggtca ttggtggagt gaagtcaaga tttccaactc      240
agtcacctga agagatggag ataccattca tggagctgga ggtccctgga gatttgggaa      300
ttcagataac aagctaagat aaggagtttg cctacctctg tcctagagcg aagcctgagc      360
cttgggcgcg cagcacacca caagtatctg ttactgtgtt ttgcagaagc ttcaggcggg      420
gatataagcc ccacaaggaa agcgctgagc agaggaggcc tcagcttgac ctgcggcagt      480
gcagcccttg ggacttccct cgccttccac ctcctgctcg tctgcttcac aagctatcgc      540
tatggtgttc gtgcgcaggc cgtggcccgc cttgaccaca gtgcttctgg ccctgctcgt      600
ctgcctaggg gcgctggtcg acgcctacca catcaaaccc gaggctcccc gcgaagacgc      660
ctcgccggag gagctgaacc gctactacgc ctccctgcgc cactacctca acctggtcac      720
ccggcagcgg tatgggaaaa gagacggccc ggacacgctt cttttccaaaa cgttcttccc      780
```

```
cgacggcgag gaccgccccg tcaggtcgcg gtcggagggc ccagacctgt ggtgaggacc      840
cctgaggcct cctgggagat ctgccaacca cgcccacgtc atttgcatac gcactcccga      900
ccccagaaac ccggattctg cctcccgacg gcggcgtctg ggcagggttc gggtgcggcc      960
ctccgcccgc gtctcggtgc ccccgccccc tgggctggag ggctgtgtgt ggtccttccc     1020
tggtcccaaa ataaagagca aattccacag aaaaaaaaaa aaaaaaaa                  1069
```

<210> SEQ ID NO 9
<211> LENGTH: 97
<212> TYPE: PRT
<213> ORGANISM: Homo sapiens

<400> SEQUENCE: 9

```
Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Arg Glu Asp Ala Ser Pro Glu Glu Leu Asn Arg Tyr
        35                  40                  45

Tyr Ala Ser Leu Arg His Tyr Leu Asn Leu Val Thr Arg Gln Arg Tyr
    50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp
```

<210> SEQ ID NO 10
<211> LENGTH: 39
<212> TYPE: PRT
<213> ORGANISM: Heloderma suspectum

<400> SEQUENCE: 10

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```